(12) United States Patent
Wertz et al.

(10) Patent No.: US 7,459,283 B2
(45) Date of Patent: *Dec. 2, 2008

(54) NANOPARTICULATE COMPOSITIONS HAVING LYSOZYME AS A SURFACE STABILIZER

(75) Inventors: Christian F. Wertz, Brookhaven, PA (US); Niels P. Ryde, Malvern, PA (US)

(73) Assignee: Elan Pharma International Limited, Dublin (IE)

( * ) Notice: Subject to any disclaimer, the term of this patent is extended or adjusted under 35 U.S.C. 154(b) by 780 days.

This patent is subject to a terminal disclaimer.

(21) Appl. No.: 10/357,514

(22) Filed: Feb. 4, 2003

(65) Prior Publication Data

US 2003/0185869 A1 Oct. 2, 2003

Related U.S. Application Data

(60) Provisional application No. 60/353,230, filed on Feb. 4, 2002.

(51) Int. Cl.
*C12Q 1/34* (2006.01)
*A61K 38/47* (2006.01)
*A61K 39/40* (2006.01)
*B82B 3/00* (2006.01)

(52) U.S. Cl. .................. 435/18; 424/94.61; 424/170; 977/739; 977/702; 977/717; 977/904; 977/914

(58) Field of Classification Search .............. 424/94.61, 424/170.1; 435/18; 977/700, 702, 705, 717, 977/737, 739, 904, 906, 915
See application file for complete search history.

(56) References Cited

U.S. PATENT DOCUMENTS

| | | | |
|---|---|---|---|
| 4,524,060 A | 6/1985 | Mughal et al. |
| 4,540,602 A | 9/1985 | Motoyama et al. |
| 4,562,069 A | 12/1985 | Hegasy et al. |
| 4,657,901 A | 4/1987 | Ueda et al. |
| 4,757,059 A | 7/1988 | Sorenson |
| 4,783,484 A | 11/1988 | Violante et al. |
| 4,814,175 A | 3/1989 | Tack et al. |
| 4,826,689 A | 5/1989 | Violanto |
| 4,997,454 A | 3/1991 | Violante et al. |
| 5,024,843 A | 6/1991 | Kuczynski et al. |
| 5,041,236 A | 8/1991 | Carpenter et al. |
| 5,145,684 A | 9/1992 | Liversidge et al. |
| 5,156,767 A | 10/1992 | Fitzgerald et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,336,662 A | 8/1994 | Lee |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,356,467 A | 10/1994 | Oshlack et al. |
| 5,399,353 A | 3/1995 | Bartnik et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,458,876 A | 10/1995 | Monticello |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,503,723 A | 4/1996 | Ruddy et al. |
| 5,506,192 A | 4/1996 | Anderson et al. |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |

(Continued)

FOREIGN PATENT DOCUMENTS

| | | |
|---|---|---|
| AU | 699996 B | 12/1998 |
| EP | 0 137 963 A1 | 4/1985 |
| EP | 0 186 118 A2 | 7/1986 |
| EP | 0 186 119 A2 | 7/1986 |
| EP | 0 186 120 A1 | 7/1986 |

(Continued)

OTHER PUBLICATIONS

Kigasawa et al., "Biopharmaceutical Studies of Drug. IV. Studies on the Improvement of Dissoultion Properties and Gastrointestinal Absorption of 2-oxo-3-[4-(1-oxo-2-Isoindolinyl)phenyl]butanamide," Database Biosis 'Online!, Biosciences Information Service, Philadelphia, PA, US; 1981, Database Accession No. PREV198274019653, XP002261016, abstract & YAKUGAKU ZASSHI, vol. 101, No. 8, 1981, pp. 723-732, XP008024282, ISSN: 0031-6903.

Kigasawa et al., "Biopharmaceutical Studies of Drugs. V. Dissolution Properties and Bioavailability of Ground Mixtures of Poorly Water Soluble Drugs and Soluble Proteins," Database CA 'Online!, Chemical Abstracts Service, Columbus Ohio, US; Database accession No. 95:156481 CA, XP002261017, abstract & YAKUGAKU ZASSHI, vol. 101, No. 8, 1981, pp. 733-739, XP008024283, ISSN: 0031-6903.

(Continued)

*Primary Examiner*—Jon P Weber
*Assistant Examiner*—Kailash C Srivastava
(74) *Attorney, Agent, or Firm*—Foley & Lardner LLP

(57) ABSTRACT

The present invention is directed to nanoparticulate active agent compositions comprising lysozyme as a surface stabilizer. Also encompassed by the invention are pharmaceutical compositions comprising a nanoparticulate active agent composition of the invention and methods of making and using such nanoparticulate and pharmaceutical compositions.

57 Claims, No Drawings

U.S. PATENT DOCUMENTS

| | | | |
|---|---|---|---|
| 5,527,545 A | 6/1996 | Santus et al. | |
| 5,534,270 A | 7/1996 | DeCastro | |
| 5,543,133 A | 8/1996 | Swanson et al. | |
| 5,552,160 A | 9/1996 | Liversidge et al. | |
| 5,560,931 A | 10/1996 | Eickhoff et al. | |
| 5,560,932 A | 10/1996 | Bagchi et al. | |
| 5,565,188 A | 10/1996 | Wong et al. | |
| 5,569,448 A | 10/1996 | Wong et al. | |
| 5,571,536 A | 11/1996 | Eickhoff et al. | |
| 5,573,749 A | 11/1996 | Illig | |
| 5,573,750 A | 11/1996 | Singh | |
| 5,573,783 A | 11/1996 | Desieno et al. | |
| 5,580,579 A | 12/1996 | Ruddy et al. | |
| 5,585,108 A | 12/1996 | Ruddy et al. | |
| 5,587,143 A | 12/1996 | Wong | |
| 5,591,456 A | 1/1997 | Franson et al. | |
| 5,593,657 A | 1/1997 | Ruddy et al. | |
| 5,608,101 A | 3/1997 | Lee et al. | |
| 5,622,938 A | 4/1997 | Wong | |
| 5,628,981 A | 5/1997 | Liversidge et al. | |
| 5,632,996 A | 5/1997 | Ramirez et al. | |
| 5,643,552 A | 7/1997 | Illig | |
| 5,662,883 A | 9/1997 | Bagchi et al. | |
| 5,665,331 A | 9/1997 | Bagchi et al. | |
| 5,718,388 A | 2/1998 | Czekai et al. | |
| 5,718,919 A | 2/1998 | Ruddy et al. | |
| 5,719,197 A | 2/1998 | Kanios et al. | |
| 5,741,522 A | 4/1998 | Violante et al. | |
| 5,747,001 A | 5/1998 | Wiedmann et al. | |
| 5,750,134 A | 5/1998 | Scholz et al. | |
| 5,756,546 A | 5/1998 | Pirotte et al. | |
| 5,776,496 A | 7/1998 | Violante et al. | |
| 5,795,909 A | 8/1998 | Shashoua et al. | |
| 5,834,025 A | 11/1998 | De Garavilla et al. | |
| 5,853,756 A | 12/1998 | Mody et al. | |
| 5,862,999 A | 1/1999 | Czekai et al. | |
| 5,904,929 A | 5/1999 | Uekama et al. | |
| 5,938,017 A | 8/1999 | Wik | |
| 5,993,781 A | 11/1999 | Snell et al. | |
| 6,001,928 A | 12/1999 | Harkness et al. | |
| 6,045,829 A | 4/2000 | Liversidge et al. | |
| 6,068,858 A | 5/2000 | Liversidge et al. | |
| 6,090,830 A | 7/2000 | Myers et al. | |
| 6,096,307 A | 8/2000 | Braswell et al. | |
| 6,117,455 A | 9/2000 | Takada et al. | |
| 6,153,225 A | 11/2000 | Lee et al. | |
| 6,165,506 A | 12/2000 | Jain et al. | |
| 6,177,103 B1 | 1/2001 | Pace et al. | |
| 6,221,400 B1 | 4/2001 | Liversidge et al. | |
| 6,239,088 B1 | 5/2001 | George et al. | |
| 6,264,922 B1 | 7/2001 | Wood et al. | |
| 6,267,989 B1 | 7/2001 | Liversidge et al. | |
| 6,270,806 B1 | 8/2001 | Liversidge et al. | |
| 6,303,147 B1 | 10/2001 | Gilis | |
| 6,316,022 B1 | 11/2001 | Mantelle et al. | |
| 6,316,029 B1 | 11/2001 | Jain et al. | |
| 6,375,986 B1 | 4/2002 | Ryde et al. | |
| 6,383,471 B1 | 5/2002 | Chen et al. | |
| 6,406,718 B1 | 6/2002 | Cooper | |
| 6,428,814 B1 | 8/2002 | Bosch et al. | |
| 6,431,478 B1 | 8/2002 | Reed et al. | |
| 6,432,381 B2 | 8/2002 | Liversidge et al. | |
| 6,579,352 B1* | 6/2003 | Tanaka et al. | 96/226 |
| 6,582,285 B2 | 6/2003 | Czekai et al. | |
| 6,592,903 B2 | 7/2003 | Ryde et al. | |
| 6,656,504 B1 | 12/2003 | Bosch et al. | |
| 6,908,626 B2 | 6/2005 | Cooper et al. | |
| 6,976,647 B2 | 12/2005 | Reed et al. | |
| 2002/0012675 A1 | 1/2002 | Jain et al. | |
| 2002/0065256 A1 | 5/2002 | Karlsson et al. | |
| 2003/0087308 A1 | 5/2003 | Lindner et al. | |
| 2003/0095928 A1* | 5/2003 | McGurk et al. | 424/46 |
| 2003/0137067 A1 | 7/2003 | Cooper et al. | |
| 2003/0181411 A1 | 9/2003 | Bosch et al. | |
| 2003/0185869 A1 | 10/2003 | Wertz et al. | |
| 2003/0215502 A1 | 11/2003 | Pruss et al. | |
| 2003/0219490 A1 | 11/2003 | Hovey et al. | |
| 2003/0224058 A1 | 12/2003 | Ryde et al. | |
| 2003/0232796 A1 | 12/2003 | Cooper et al. | |
| 2004/0018242 A1 | 1/2004 | Cunningham et al. | |
| 2004/0033202 A1 | 2/2004 | Cooper et al. | |
| 2004/0033267 A1 | 2/2004 | Merisko-Liversidge et al. | |
| 2004/0058009 A1 | 3/2004 | Ryde et al. | |
| 2004/0087656 A1 | 5/2004 | Ryde et al. | |
| 2004/0101566 A1* | 5/2004 | Cooper et al. | 424/489 |
| 2004/0105778 A1 | 6/2004 | Lee et al. | |
| 2004/0105889 A1 | 6/2004 | Ryde et al. | |
| 2004/0115134 A1 | 6/2004 | Merisko-Liversidge | |
| 2004/0141925 A1 | 7/2004 | Bosch et al. | |
| 2004/0156872 A1 | 8/2004 | Bosch et al. | |
| 2004/0156895 A1 | 8/2004 | Pruitt et al. | |
| 2004/0164194 A1 | 8/2004 | Reed et al. | |
| 2004/0173696 A1 | 9/2004 | Cunningham et al. | |
| 2004/0208833 A1 | 10/2004 | Hovey et al. | |
| 2004/0229038 A1 | 11/2004 | Cooper et al. | |
| 2004/0258757 A1 | 12/2004 | Bosch et al. | |
| 2004/0258758 A1 | 12/2004 | Gustow et al. | |
| 2005/0004049 A1 | 1/2005 | Liversidge | |
| 2005/0008707 A1 | 1/2005 | Hovey et al. | |
| 2005/0019412 A1 | 1/2005 | Bosch et al. | |
| 2005/0031691 A1 | 2/2005 | McGurk et al. | |
| 2005/0042177 A1 | 2/2005 | Ryde et al. | |
| 2005/0063913 A1 | 3/2005 | Pruitt et al. | |
| 2005/0147664 A1 | 7/2005 | Liversidge et al. | |
| 2005/0233001 A1 | 10/2005 | Hovey et al. | |
| 2005/0238725 A1 | 10/2005 | Cunningham et al. | |
| 2005/0244503 A1 | 11/2005 | Rabinow et al. | |

FOREIGN PATENT DOCUMENTS

| | | |
|---|---|---|
| EP | 0 249 150 B1 | 12/1987 |
| EP | 0 315 589 B1 | 5/1989 |
| EP | 0 336 898 A2 | 10/1989 |
| EP | 0 394 889 A2 | 10/1990 |
| EP | 0 461 079 B1 | 12/1991 |
| EP | 0 499 299 B1 | 8/1992 |
| EP | 0 506 967 A1 | 10/1992 |
| EP | 0 549 524 A1 | 6/1993 |
| EP | 0 577 215 B1 | 1/1994 |
| EP | 0 601 619 A2 | 6/1994 |
| EP | 0 602 702 B1 | 6/1994 |
| EP | 0 990 437 A | 4/2000 |
| GB | 2088877 | 6/1982 |
| GB | 2 166 651 A | 5/1986 |
| JP | 57-26615 A | 2/1982 |
| WO | WO 91/10653 A1 | 7/1991 |
| WO | WO 96/03132 | 2/1996 |
| WO | WO 96/03132 A1 | 2/1996 |
| WO | WO 98/07414 A1 | 2/1998 |
| WO | WO 00/72973 A1 | 12/2000 |
| WO | WO 02/098565 A1 | 12/2002 |

OTHER PUBLICATIONS

Guidance for Industry, Levothyroxine Sodium Tablets-In Vivo Pharmacokinetic and Bioavailability Studies and in Vitro Dissolution Testing, U.S. Department of Health and Human Services, Food and Drug Administration, Dec. 2000, pp. 1-8.

*Physician's Desk Reference*, 57th Edition, pp. 1433, 1438, 1497, 1522, 1525, 1528, 1532 (2003).

Lindahl et al., "Characterization of Fluids from the Stomach and Proximal Jejunum in Men and Women", *Pharmaceutical Research*, vol. 14, No. 4, pp. 497-502, 1997.

* cited by examiner

NANOPARTICULATE COMPOSITIONS HAVING LYSOZYME AS A SURFACE STABILIZER

FIELD OF THE INVENTION

The present invention is directed to nanoparticulate formulations of an active agent having lysozyme adsorbed onto or associated with the surface of the agent as a surface stabilizer, and methods of making and using such compositions.

BACKGROUND OF THE INVENTION

A. Background Regarding Nanoparticulate Compositions

Nanoparticulate compositions, first described in U.S. Pat. No. 5,145,684 ("the '684 patent"), are particles consisting of a poorly soluble therapeutic or diagnostic agent having adsorbed onto, or associated with, the surface thereof a non-crosslinked surface stabilizer. The '684 patent describes the use of a variety of surface stabilizers for nanoparticulate compositions. The use of a lysozyme as a surface stabilizer for nanoparticulate compositions, or any other component of such compositions, is not described by the '684 patent.

The '684 patent describes a method of screening active agents to identify useful surface stabilizers that enable the production of a nanoparticulate composition. Not all surface stabilizers will function to produce a stable, non-agglomerated nanoparticulate composition for all active agents. Moreover, known surface stabilizers may be unable to produce a stable, non-agglomerated nanoparticulate composition for certain active agents. Thus, there is a need in the art to identify new surface stabilizers useful in making nanoparticulate compositions. Additionally, such new surface stabilizers may have superior properties over prior known surface stabilizers.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive nanoparticulate compositions having cationic surface stabilizers;" U.S. Pat. No. 6,431,478 for "Small Scale Mill;" and U.S. Pat. No. 6,432,381 for "Methods for targeting drug delivery to the upper and/or lower gastrointestinal tract," all of which are specifically incorporated by reference. In addition, U.S. patent application No. 20020012675 A1, published on Jan. 31, 2002, for "Controlled Release Nanoparticulate Compositions," describes nanoparticulate compositions, and is specifically incorporated by reference.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

B. Background Regarding the Use of Lysozyme in Pharmaceutical Compositions

Lysozyme, also known as muramidase, N-acetylmuramylhydrolase, and globulin G1, has a molecular weight of about 14,400. It is a mucolytic enzyme with antibiotic properties first discovered by A. Fleming, *Proc. Roy. Soc. London*, 93B: 306 (1922). Lysozyme is found in tears, nasal mucus, milk, saliva blood serum, a great number of tissues and secretions of different animals, vertebrates and invertebrates, egg white, some molds, and in the latex of different plants.

The structure of lysozyme consists of a single polypeptide linked by four disulfide bridges. It lyses bacterial cell wall polysaccharides by hydrolyzing the 1,4-β-linkages between N-acetylmuramic acid and N-acetyl-D-glucosamine residues.

Although lysozyme has antibiotic properties, it is a large molecule that is not particularly useful as a drug. It can be applied topically, but cannot rid the entire body of disease because it is too large to travel between cells.

A number of U.S. patents describe the use of lysozyme as an active ingredient in pharmaceutical compositions. See e.g., U.S. Pat. No. 6,096,307 for "Compositions for Immunostimulation Containing Echinacea Angustofolia, Bromelain, and Lysozyme," U.S. Pat. No. 6,239,088 for "Nonirritating Cleansing Composition," U.S. Pat. No. 5,458,876 for "Control of Microbial Growth with Antibiotic/lysozyme Formulations," and U.S. Pat. No. 5,041,236 for "Antimicrobial Methods and Compositions Employing Certain Lysozymes and Endoglycosidases."

There is a need in the art for new surface stabilizers useful in preparing nanoparticulate compositions of active agents. The present invention satisfies this need.

SUMMARY OF THE INVENTION

The present invention is directed to nanoparticulate compositions comprising a poorly soluble active agent and lysozyme as a surface stabilizer adsorbed on to, or associated with, the surface of the active agent.

Another aspect of the invention is directed to pharmaceutical compositions comprising a nanoparticulate composition of the invention. The pharmaceutical compositions preferably comprise a poorly soluble active agent, lysozyme, and a pharmaceutically acceptable carrier, as well as any desired excipients.

In yet another embodiment, the invention is directed to bioadhesive nanoparticulate compositions comprising lysozyme. Such compositions can coat the gut, or the desired site of application, and be retained for a period of time, thereby increasing the efficacy of the active agent as well as eliminating or decreasing the frequency of dosing.

This invention further discloses a method of making a nanoparticulate composition having a lysozyme surface stabilizer adsorbed on or associated with the surface of the active agent. Such a method comprises contacting a poorly soluble nanoparticulate active agent with lysozyme for a time and under conditions sufficient to provide a nanoparticle/ lysozyme composition. The lysozyme surface stabilizer can be contacted with the active agent either before, during, or after size reduction of the active agent.

The present invention is further directed to a method of treatment comprising administering to a mammal a therapeutically effective amount of a nanoparticulate active agent/ lysozyme composition according to the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is directed to compositions comprising nanoparticulate active agents having lysozyme as a surface stabilizer adsorbed on or associated with the surface thereof, and methods of making and using such nanoparticulate compositions.

As taught in the '684 patent, not every combination of surface stabilizer and active agent will result in a stable nanoparticulate composition. The discovery of the present invention is even more surprising as other protein surface stabilizers were found to be ineffective in attempts to make nanoparticulate compositions of varying drug classes and structures. Such ineffective protein stabilizers include fibrinogen, γ-globulin, albumin, and casein.

Moreover, an unexpected benefit of the nanoparticulate compositions of the invention is that the compositions are likely to exhibit bioadhesive properties. This is because lysozyme has a high isoelectric point (pI=11.35), which will likely result in stable nanoparticulate compositions exhibiting relatively large, positive zeta potentials. To increase the bioadhesive properties of a nanoparticulate composition, one or more cationic surface stabilizers can be utilized.

Bioadhesive formulations of nanoparticulate active agents comprising lysozyme exhibit exceptional bioadhesion to biological surfaces, such as mucous, skin, etc. The term bioadhesion refers to any attractive interaction between two biological surfaces or between a biological and a synthetic surface. In the case of bioadhesive nanoparticulate compositions, the term bioadhesion is used to describe the adhesion between the nanoparticulate compositions and a biological substrate (i.e. gastrointestinal mucin, lung tissue, nasal mucosa, etc.). See e.g., U.S. Pat. No. 6,428,814 for "Bioadhesive Nanoparticulate Compositions Having Cationic Surface Stabilizers," which is specifically incorporated by reference. There are basically two mechanisms which may be responsible for this bioadhesion phenomena: mechanical or physical interactions and chemical interactions. The first of these, mechanical or physical mechanisms, involves the physical interlocking or interpenetration between a bioadhesive entity and the receptor tissue, resulting from a good wetting of the bioadhesive surface, swelling of the bioadhesive polymer, penetration of the bioadhesive entity into a crevice of the tissue surface, or interpenetration of bioadhesive composition chains with those of the mucous or other such related tissues. The second possible mechanism of bioadhesion incorporates forces such as ionic attraction, dipolar forces, van der Waals interactions, and hydrogen bonds. It is this form of bioadhesion which is primarily responsible for the bioadhesive properties of the nanoparticulate compositions of the invention. However, physical and mechanical interactions may also play a secondary role in the bioadhesion of such nanoparticulate compositions.

The bioadhesive nanoparticulate active agent compositions of the invention are useful in any situation in which it is desirable to apply the compositions to a biological surface. The bioadhesive nanoparticulate active agent compositions of the invention coat the targeted surface in a continuous and uniform film which is invisible to the naked human eye.

In addition, a bioadhesive formulation slows the transit of the formulation, and some active agent particles would also most likely adhere to other tissue than the mucous cells and therefore give a prolonged exposure to the active agent.

The adhesion exhibited by the inventive compositions means that nanoparticulate active agent particles are not easily washed off, rubbed off, or otherwise removed from the biological surface for an extended period of time. The period of time in which a biological cell surface is replaced is the factor that limits retention of the bioadhesive nanoparticulate active agent particles to that biological surface. For example, skin cells are replaced every 24-48 hours. Thus, the nanoparticulate active agent composition would have to be reapplied to the skin every 48 hours. Mucous cells shed and are replaced about every 5-6 hours.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein with reference to stable drug particles, 'stable' means that drug particles do not appreciably flocculate or agglomerate due to interparticle attractive forces or otherwise increase in particle size.

'Therapeutically effective amount' as used herein with respect to a drug dosage, shall mean that dosage that provides the specific pharmacological response for which the drug is administered in a significant number of subjects in need of such treatment. It is emphasized that 'therapeutically effective amount,' administered to a particular subject in a particular instance will not always be effective in treating the diseases described herein, even though such dosage is deemed a 'therapeutically effective amount' by those skilled in the art. It is to be further understood that drug dosages are, in particular instances, measured as oral dosages, or with reference to drug levels as measured in blood.

A. Compositions

The compositions of the invention comprise a nanoparticulate active agent and lysozyme as a surface stabilizer adsorbed to or associated with the surface of the active agent. In addition, the compositions can comprise one or more secondary surface stabilizers. Surface stabilizers useful herein physically adhere to the surface of the nanoparticulate active agent but do not chemically react with the active agent or itself. Individually molecules of the surface stabilizer are essentially free of intermolecular cross-linkages.

The present invention also includes nanoparticulate compositions having lysozyme as a stabilizer adsorbed on or associated with the surface thereof, formulated into compositions together with one or more non-toxic physiologically acceptable carriers, adjuvants, or vehicles, collectively referred to as carriers. The compositions can be formulated for parenteral injection, oral administration in solid, liquid, or aerosol form, rectal or topical administration, and the like.

1. Active Agent Particles

The nanoparticles of the invention comprise an active, therapeutic, or diagnostic agent, collectively referred to as a "drug." A therapeutic agent can be a pharmaceutical agent, including biologics such as proteins, peptides, and nucleotides, or a diagnostic agent, such as a contrast agent, including x-ray contrast agents. The active agent exists either as a discrete, crystalline phase, an amorphous phase, a semi-amorphous phase, a semi-crystalline phase, or mixtures thereof. The crystalline phase differs from a non-crystalline or amorphous phase which results from precipitation techniques, such as those described in EP Pat. No. 275,796. Two or more active agents can be used in combination.

The invention can be practiced with a wide variety of active agents. The active agent is preferably present in an essentially pure form, is poorly soluble, and is dispersible in at least one liquid dispersion medium. By "poorly soluble" it is meant that the active agent has a solubility in the liquid dispersion medium of less than about 10 mg/mL, and preferably of less than about 1 mg/mL. Useful liquid dispersion mediums include, but are not limited to, water, aqueous salt solutions, safflower oil, and solvents such as ethanol, t-butanol, hexane, and glycol.

a. Active Agents Generally

The active agent can be selected from a variety of known classes of drugs, including, for example, proteins, peptides, nucleotides, anti-obesity drugs, nutraceuticals, dietary supplements, carotenoids, corticosteroids, elastase inhibitors, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

Active agents to be administered in an aerosol formulation are preferably selected from the group consisting of proteins, peptide, bronchodilators, corticosteroids, elastase inhibitors, analgesics, anti-fungals, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, fungal infection therapies, respiratory illness therapies associated with acquired immune deficiency syndrome, an oncology drug, an anti-emetic, an analgesic, and a cardiovascular agent.

A description of these classes of active agents and a listing of species within each class can be found in Martindale, *The Extra Pharmacopoeia*, Twenty-ninth Edition (The Pharmaceutical Press, London, 1989), specifically incorporated by reference. The active agents are commercially available and/or can be prepared by techniques known in the art.

b. Active Agents Useful in Dermal Applications

The active agents according to the present invention include, but are not limited to, active agents which can be used in dermal applications, e.g., sunscreens, cosmetics, topical application of pharmaceuticals to the dermis (acne medication, anti-wrinkle drugs, such as alpha-hydroxy formulations), nail polish, moisturizers, deodorant, etc.

Cosmetic compositions are generally defined as compositions suitable for application to the human body. Cosmetic compositions such as creams and lotions are used to moisturize the skin and keep it in a smooth, supple condition. Pigmented cosmetic compositions, such as makeup, blush, lipstick, and eye shadow, are used to color the skin and lips. Since color is one of the most important reasons for wearing cosmetics, color-containing cosmetics must be carefully formulated to provide maximum wear and effect.

One of the long standing problems with pigmented cosmetic compositions, such as face makeup, lipstick, mascara, and the like, is the tendency of the cosmetic to blot or transfer from the skin or lashes onto other surfaces, such as glassware, silverware, or clothing. This blotting not only creates soiling but it also forces the cosmetic user to reapply cosmetic at fairly short intervals.

Traditional pigmented cosmetic compositions are either water and oil emulsions containing pigments, or they are anhydrous systems containing waxes, oils, and pigments. These formulations are applied and blended into the skin to provide color and to correct skin topography to provide an even, smooth appearance. The films are simply deposited on the surface of the skin and if touched with fingers the product may transfer or become blotchy and uneven. Perspiration or sebum will break through the film and cause running or smearing. If skin comes into contact with clothing, the clothing may become soiled.

Other areas which benefit from the present invention include coloring agents, flavors, and fragrances. Coloring agents or pigments are used in cosmetic applications as well as in fabric applications. Suitable pigments can be inorganic and/or organic. Also included within the term pigment are materials having a low color or luster, such as matte finishing agents, and also light scattering agents. Examples of suitable pigments are iron oxides, acylglutamate iron oxides, ultramarine blue, D&C dyes, carmine, and mixtures thereof. Depending upon the type of cosmetic composition, e.g., foundation or blusher, a mixture of pigments will normally be used.

Bioadhesive nanoparticulate cosmetic compositions satisfy a long-felt need for cosmetic compositions that strongly adhere to the biological surface to which they are applied.

Fragrances and odiferous compounds are also suitable for use in the present inventive compositions. Bioadhesive nanoparticulate compositions comprising a fragrance or odiferous compound as an active agent could provide prolonged sensory stimulation following application; i.e., for up to 48 hours following application to the skin.

c. Active Agents Useful in Mucous Applications

Exemplary active agents to be applied to mucous include dental applications, such as oral bioadhesive nanoparticulate lidocain formulations, bioadhesive nanoparticulate fluoride treatments, application to the lungs, throat, GIT, application to wounds, etc. Also included is application to the throat using a liquid containing a bioadhesive nanoparticulate formulation containing, for example, menthol or other numbing compound for treatment of coughs or sore throats. The stomach and GIT can also be treated using bioadhesive formulations. This is particularly useful for treatment of diseases associated with the mucous of the gastrointestinal tract, such as Crohn's Disease. Other pharmaceutical therapeutic methodologies include oral dosing, nasal administration, vaginal administration, ocular administration, colonic, and subcutaneous administration.

The compositions of the invention also encompass food products. For example, spice, oleoresin, flavor oil, color, or chemicals are often added during food processing to produce the desirable flavors, taste, and appearance. These agents can be included in a bioadhesive nanoparticulate composition of the present invention for increased adhesion to biological surfaces. Bioadhesive nanoparticulate flavoring agents could be used in products such as gums to produce prolonged flavor.

d. Active Agents Useful in Hair Applications

Biological substrates such as the hair are also encompassed by the scope of the invention. Bioadhesive nanoparticulate compositions can be used in hair conditioner formulations, hair dyes, hair sprays, hair cosmetics, hair cleansers, depilatories, etc.

e. Active Agents Useful in Plant Tissue Applications

Yet another area of applicability of the present invention includes bioadhesive nanoparticulate compositions that can be applied to plant tissue. Because of the difficulty in solubilizing some agricultural agents (i.e., some agricultural agents are applied as insoluble powders), the present invention provides a superior application method for plants as compared to prior art plant application methods.

Bioadhesive nanoparticulate compositions can be used for applications of pesticides, insecticides, fertilizers, etc.—any substance to be applied to the surface of a plant. All plants, such as grass, trees, commercial farm crops (such as corn, soybeans, cotton, vegetables, fruit, etc), weeds, etc., are encompassed by the scope of this invention.

In one embodiment of the invention, the active agent of the bioadhesive nanoparticulate composition is an insecticidal ingredient applied to seeds, plants, trees, harvested crops, soil, and the like. The insecticide ingredient can be selected from a wide variety of organic compounds or mixtures which are known and used in agriculture and horticulture applications, such as those listed in W. T. Thomson, *Agricultural Chemicals, Book I, Insecticides* (Thomson Publications, Fresno, Calif. 1989).

The general categories of insecticidal-active organic compounds include chlorinated hydrocarbon derivatives, phosphorated derivatives, pyrethroids, acylureas, and the like. Chlorinated hydrocarbon insecticides usually act as stomach and contact poisons affecting the nervous system. They are persistent in the environment and tend to accumulate in animal fatty tissue, as exemplified by DDT and chlordane.

Illustrative of other insecticidal compounds are chlorfluazuron, chlorpyrifos, chlorpyrifos methyl, bromophos, diazinon, malathion, trichlorfon, dimethoate, phorate, lindane, toxaphene, diflubenuron, methomyl, propoxur, carbaryl, cyhexatin, cypermethrin, permethrin, fenvalerate, dicofol, tetradifon, propargite, and the like. Other examples of insecticides include the pyrethroid insecticides, such a Fenvalerate™ [α-cyano-3-phenoxybenzyl-2-(4-chlorophenyl)-3methylvalerate] and Pyrethroid™ [cyano(4-fluoro-3-phenoxyphenymethl-3-(2,2-dichloroethenyl)-2,2-dimethyl cyclopropanecarboxylate]; organophosphorus insecticides, such as DDVP™ (2,2-dichlorovinyldimethyl phosphate), Sumithion™ (dimethyl-4-nitro-m-tolylphosphorothionate), Malathone™ {S-[1,2-bis(ethoxycarbonyl)ethyl]dimethylphosphorothiol thionate}, Dimethoate [dimethyl-S-(N-methylcarbamolymethyl)-phosphorothios thionate), Elsan™ {S-[.alpha.-(ethoxycarbonyl)benzyl]dimethylphosphorothiol thionate), and Baycid™ [O,O-dimethyl-O-(3-methyl-4methylmercaptophenyl)thiophosphate]; carbamate; insecticides such as Bassa™ (O-butylphenyl methylcarbamate), MTMC™ (m-tolyl methylcarbamate), Meobal™ (3,4-dimethylphenyl-N-methylcarbamate), and NAC™ (1-naphthyl-N-methylcarbamate; as well as Methomyl™ {methyl-N [(methylcarbamoyl)-oxy]thioacetimide }, and Cartap™ {1,3-bis(carbamolythio)-2-(N,N-dimethylamino)propane hydrochloride}.

Examples of other agricultural agents include acaricides such as, but not limited to, Smite™ {2-[2-(p-tert-butylphenoxy)isopropoxy]isopropyl-2-chloroethyl sulfide }, Acricid™ (2,4-dinitro-6-sec-butylphenyl dimethylacrylate), Chlormit™ (isopropyl 4,4-dichlorobenzylate), Acar™ (ethyl 4,4-dichlorobenzylate), Kelthane™ [1,1-bis(p-chlorophenyl-2,2,2-trichloroethanol], Citrazon™ (ethyl O-benzoyl-3-chloro-2,6-dimethoxybenzohydroxymate), Plictran™ (tricyclohexyltin hydroxide), and Omite™ [2-(p-tert-butylphenoxy)cyclohexyl-2-propinyl sulfite].

Examples of germicides include organosulfur germicides, such as Dithane™ (zinc ethylenebisdithiocarbamate), Maneo™ (manganese ethylenebis-dithiocarbamate), Thiuram™ [bis(dimethylthiocarbamoyl) disulfide ], Benlate™ [methyl 1-(butylcarbamoyl-2-benzimidazole carbamate], Difolatan™ (N-tetrachloroethylthio-4-cyclohexane-1,2-dicarboxyimide), Daconol™ (tetrachloroisophthalonitrile), Pansoil™ (5-ethoxy-3-trichloromethyl-1,2,4-thiadiazole), Thiophanate-methyl [1,2-bis(3-methoxycarbonyl-2-thioureido)benzene], Rabcide™ (4,5,6,7-tetrachlorophthaloid), Kitazin P™ (O,O-diisopropyl-S-benzyl phosphorothioate), Hinonsan™ (O-ethyl-S,S-diphenydithiophosphate), and Propenazol™ (3-allyloxy-1,2-benzothiazole 1,1-dioxide).

Example of plant growth regulating agents include, but are not limited to, MH™ (maleic acid hydrazide) and Ethrel™ (2-chloroethylphosphonic acid).

Examples of herbicides include, but are not limited to Stam™ (3,4-dichloropropionanilide), Saturn™ [S-(4-chlorobenzyl) N,N-diethylthiolcarbamate), Lasso (2-chloro-2',6'-diethyl-N-(methoxymethyl)acetanilide), Glyphosate™ [N-(phosphonomethyl)glycine isopropylamine salt], DCMU[3-(3,4-dichlorophenyl)-1,1-dimethylurea), and Gramoxone™ (1,1'-dimethyl-4,4'-dipyridium dichloride].

Other herbicides contemplated for use in the present invention include auxin transport inhibitors, e.g., naptalam; growth regulators, including benzoic acids, e.g., dicamba; phenoxy acids, such as (i) acetic acid type, e.g., 2,4-D, MCPA, (ii) propionic acid type, e.g., 2,4-DP, MCPP, and (iii) butyric acid type, e.g., 2,4-DB, MCPB; picolinic acids and related compounds, e.g., picloram, triclopyr, fluroxypyr, and clopyralid.

Photosynthesis inhibitors are also herbicides useful in the compositions of the invention. Such compounds include but are not limited to (a) s-triazines, such as (i) chloro substituted, e.g., atrazine, simazine, and cyanazine, (ii) methoxy substituted, e.g., prometon, (iii) methylthio substituted, e.g., ametryn and prometryn; (b) other triazines, such as hexazinone, and metribuzin; (c) substituted ureas, such as diuron, fluometuron, linuron, tebuthiuron, thidiazuron, and forchlorfenuron; (d) uracils, such as bromacil and terbacil; and (e) others, such as bentazon, desmedipham, pheninedipham, propanil, pyrazon, and pyridate.

Pigment inhibitors are also herbicides useful in the compositions of the invention. Such compounds include but are not limited to pyridazinones, such as norflurazon; isoxazolones, such as clomazone; and others, such as amitrole and fluridone.

In yet another aspect of the invention, growth inhibitors are herbicides useful in the compositions of the invention. Such compounds include but are not limited to (a) mitotic disruptors, such as (i) dinitroanilines, e.g., trifluralin, prodiamine, benefin, ethalfluralin, isopropalin, oryzalin, and pendimethalin; and (ii) others, such as DCPA, dithiopyr, thiazopyr, and pronamide; (b) inhibitors of shoots of emerging seedlings, such as (i) thiocarbamates, e.g., EPTC, butylate, cycloate, molinate, pebulate, thiobencarb, triallate, and vernolate; (c) inhibitors of roots only of seedlings, such as bensulide, napropamide, and siduron; and (d) inhibitors of roots and shoots of seedlings, including chloroacetamides, such as alachlor, acetochlor, metolachlor, diethatyl, propachlor, butachlor, pretilachlor, metazachlor, dimethachlor, and cinmethylin.

Amino acid synthesis inhibitors are herbicides useful in the compositions of the invention. Such compounds include, but are not limited to, (a) glyphosate, glufosinate; (b) sulfonylureas, such as rimsulfuron, metsulfuron, nicosulfuron, triasulfuron, primisulfuron, bensulfuron, chlorimuron, chlorsulfuron, sulfometuron, thifensulfuron, tribenuron, ethametsulfuron, triflusulfuron, clopyrasulfuron, pyrazasulfuron, prosulfuron (CGA-152005), halosulfuron, metsulfuron-methyl, and chlorimuron-ethyl; (c) sulfonamides, such as flumetsulam (a.k.a. DE498); (d) imidazolinones, such as imazaquin, imazamethabenz, imazapyr, imazethapyr, and imazmethapyr.

Lipid biosynthesis inhibitors are herbicides useful in the compositions of the invention. Such compounds include, but are not limited to, (a) cyclohexanediones, such as sethoxydim and clethodim; (b) aryloxyphenoxys, such as fluazifop-(P-butyl), diclofop-methyl, haloxyfop-methyl, and quizalofop; and (c) others, such as fenoxaprop-ethyl.

Cell wall biosynthesis inhibitors are herbicides useful in the compositions of the invention. Such compounds include, but are not limited to, dichlobenil and isoxaben.

Rapid cell membrane disruptors are herbicides useful in the compositions of the invention. Such compounds include, but are not limited to, (a) bipyridiliums, such as paraquat, and diquat; (b) diphenyl ethers, such as acifluorfen, fomesafen, lactofen, and oxyfluorfen; (c) glutamine synthetase inhibitors, such as glufosinate; and (d) others, such as oxadiazon.

Miscellaneous herbicides useful in the compositions of the invention include, but are not limited to, (a) carbamates, such as asulam; (b) nitriles, such as bromoxynil and ioxynil; (c) hydantocidin and derivatives; and (d) various other compounds, such as paclobutrazol, ethofumesate, quinclorac (a.k.a. BAS514), difenzoquat, endothall, fosamine, DSMA, and MSMA.

Other herbicides useful in the compositions of the invention include, but are not limited to, triketones and diones of the type described in U.S. Pat. Nos. 5,336,662 and 5,608,101, the contents of each of which are incorporated herein by reference, and in EP-A-338-992; EP-A-394-889; EP-A-506, 967; EP-A-137,963; EP-A-186-118; EP-A-186-119; EP-A-186-120; EP-A-249-150; and EP-A-336-898. Examples of such triketones and diones are sulcotrione (MIKADO™), whose chemical designation is 2-(2-chloro-4-methanesulfonylbenzoyl)-1,3-cyclohexanedione: 2-(4-methylsulfonyloxy-2-nitrobenzoyl)-4,4,6,6-tetramethyl-1,3-cyclohexane dione; 3-(4-methylsulfonyloxy-2-nitrobenzoyl)-biyclo[3,2,1]octane-2,4-dione3-(4-methylsulfonyl-2-nitrobenzoyl)-bicyclo[3,2,1]octane-2,4-dione; 4-(4-chloro-2-nitrobenzoyl)-2,6,6-trimethyl-2H-1,2-oxazine-3,5(4H,6H)dione; 4-(4-methylthio-2-nitrobenzoyl)-2,6,6-trimethyl-2H-1,2-oxazine-3,5(4H,6H)-dione; 3-(4-methylthio-2-nitrobenzoyl)-bicyclo[3,2,1]octane-2,4-dione; 4-(2-nitro-4-trifluoromethoxybenzoyl)-2,6,6-trimethyl-2H-1,2-oxazine-3,5(4H,6H)-dione.

Herbicidal compounds useful in the nanoparticulate compositions of the invention are described in U.S. Pat. No. 5,506,192; EP-A-461,079; EP-A-549,524; EP-A-315,589 and PCT Appln. No. 91/10653. The contents of all of the cited references are incorporated herein by reference; including for example 3-[(4,6-dimethoxy-2-pyrimidinyl)hydroxymethyl]-N-methyl-2-pyridine carboxamide; 4,7-dichloro-3-(4,6-dimethoxy-2-pyrimidinyl)-3-hexanoyloxyphthalide; 3-[(4,6-dimethoxy-2-pyrimidinyl)carbonyl]-N,N-dimethyl-2-pyridine carboxamide; 3,6-dichloro-2-[(4,6-dimethoxy-2-pyrimidinyl)carbonyl]benzoic acid; 6-chloro-2-[(4,6-dimethoxy-2-pyrimidinyl)thio]benzoic acid (a.k.a. DPX-PE350 or pyrithiobac) and salts thereof.

f. Active Agents in Miscellaneous Applications

Other exemplary uses of the novel bioadhesive formulations are provided: teeth can be treated with teeth whiteners or fluoride bioadhesive compositions; bones can be treated with calcium bioadhesive compositions; nails can be treated with color or strengthening bioadhesive formulations; insects or pests can be treated with insecticides or other toxic compositions to the pest. In sum, the compositions are useful in treating any biological surface, or a surface derived from a biological material. Feathers and scales of animals can be treated, as well as other animal biological surfaces such as chitin.

2. Lysozyme Surface Stabilizer

The choice of a surface stabilizer is non-trivial and usually requires extensive experimentation to realize a desirable formulation. Accordingly, the present invention is directed to the surprising discovery that lysozyme, used as a nanoparticulate surface stabilizer, yields stable nanoparticulate compositions that exhibit low degrees of aggregation. This discovery is particularly unexpected as it was found that nanoparticulate compositions employing other protein surface stabilizers, such as casein, albumin, γ-globulin, and fibrinogen, give rise to unstable dispersions with concomitant and severe aggregation.

An unexpected benefit of the nanoparticulate compositions of the invention is that the compositions are likely to exhibit bioadhesive properties. This is because lysozyme has a high isoelectric point (pI=11.35), which will likely result in stable nanoparticulate compositions exhibiting relatively large, positive zeta potentials.

3. Auxiliary Surface Stabilizers

The compositions of the invention can also include one or more auxiliary or secondary surface stabilizers in addition to lysozyme. Suitable auxiliary surface stabilizers can preferably be selected from known organic and inorganic pharmaceutical excipients. Such excipients include various polymers, low molecular weight oligomers, natural products, and surfactants. Preferred surface stabilizers include nonionic, ionic, cationic, and zwitterionic surfactants. Two or more surface auxiliary stabilizers can be used in combination.

Depending upon the desired method of administration, bioadhesive formulations of nanoparticulate compositions can be prepared by selecting one or more cationic surface stabilizers that impart bioadhesive properties to the resultant composition.

Representative examples of auxiliary surface stabilizers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxes 3350® and 1450®, and Carbopol 934® (Union Carbide)), dodecyl trimethyl ammonium bromide, polyoxyethylene stearates, colloidal silicon dioxide, phosphates, sodium dodecylsulfate, carboxymethylcellulose calcium, hydroxypropyl celluloses (e.g., HPC, HPC-SL, and HPC-L), hydroxypropyl methylcellulose (HPMC), carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1, 1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, sodium lauryl sulfate, dioctylsulfosuccinate (DOSS); Tetronic 1508® (T-1508) (BASF Wyandotte Corporation ), dialkylesters of sodium sulfosuccinic acid (e.g., Aerosol OT®, which is a dioctyl ester of sodium sulfosuccinic acid (Cytec Industries, West Paterson, N.J.)); Duponol P®, which is a sodium lauryl sulfate (DuPont); Triton X-200®, which is an alkyl aryl polyether sulfonate (Union Carbide); Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); decanoyl-N-methylglucamide; n-decyl β-D-glucopyranoside; n-decyl β-D-maltopyransoide; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glycopyranoside; octanoyl-N-methylglucamide; n-octyl-β-D-glucopyranoside; octyl β-D-thioglucopyranoside; random copolymers of vinyl acetate and vinyl pyrrolidone, and the like. Two or more surface stabilizers can be used in combination.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide(PMMTMABr), hexyldesyltrimethylammonium bromide(HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt) (also known as DPPE-PEG (2000)-Amine Na) (Avanti Polar Lipids, Alabaster, Ala.), Poly(2-methacryloxyethyl trimethylammonium bromide) (Polysciences, Inc., Warrington, Pa.) (also known as S1001), poloxamines such as Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.), lysozyme, long-chain polymers such as alginic acid, carrageenan (FMC Corp.), and POLYOX (Dow, Midland, Mich.).

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ammonium chloride or bromide, N-alkyl ($C_{12-18}$) dimethylbenzyl ammonium chloride, N-alkyl($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$)dimethyl1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$)dimethyl1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$trimethyl ammonium bromides, dodecylbenzyl triethyl ammonium chloride, poly-diallyldimethylammonium chloride(DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride(ALIQUAT 336™), POLYQUAT10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric cationic surface stabilizers are any nonpolymeric compound, such as benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;

(xi) two of $R_1$-$R_4$ are $CH_3$ and one of $R_1$-$R_4$ is a phenyl ring; or (xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride(Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE(10)oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediarnine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference. The surface stabilizers are commercially available and/or can be prepared by techniques known in the art.

4. Nanoparticulate Active Agent/Lysozyme Particle Size

The compositions of the invention contain nanoparticulate active agent particles which have an effective average particle size of less than about 2000 nm (i.e., 2 microns), less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% by weight of the active agent particles have a particle size less than the effective average, i.e., less than about 2000 nm, 1900 nm, 1800 nm, etc., when measured by the above-noted techniques. In other embodiments of the invention, at least about 70%, at least about 90%, or at least about 95% of the active agent particles have a particle size less than the effective average, i.e., less than about 2000 nm, 1900 nm, 1800 nm, etc.

5. Concentration of Nanoparticulate Active Agent and Stabilizer

The relative amounts of active agent and lysozyme, and optionally one or more secondary surface stabilizers, can vary widely. The optimal amount of the individual components can depend, for example, upon the particular active agent selected, the hydrophilic lipophilic balance (HLB), melting point, and the surface tension of water solutions of the stabilizer, etc.

The concentration of lysozyme can vary from about 0.5% to about 99.999%, from about 5.0% to about 99.9%, or from about 10% to about 99.5%, by weight, based on the total combined dry weight of the at least one active agent and lysozyme, not including other excipients.

The concentration of the active agent can vary from about 99.5% to about 0.001%, from about 95% to about 0.1%, or from about 90% to about 0.5%, by weight based on the total combined dry weight of the active agent and surface stabilizer, not including other excipients.

B. Methods of Making Nanoparticulate Formulations

The nanoparticulate active agent compositions can be made using, for example, milling, homogenization, or precipitation techniques. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

The resultant nanoparticulate active agent compositions can be utilized in solid or liquid dosage formulations, such as controlled release formulations, solid dose fast melt formulations, aerosol formulations, nasal formulations, lyophilized formulations, tablets, capsules, solid lozenge, powders, creams, ointments, etc.

1. Milling to Obtain Nanoparticulate Active Agent Dispersions

Milling the active agent to obtain a nanoparticulate dispersion comprises dispersing active agent particles in a liquid dispersion medium in which the active agent is poorly soluble, followed by applying mechanical means in the presence of grinding media to reduce the particle size of the active agent to the desired effective average particle size. The dispersion medium can be, for example, water, safflower oil, ethanol, t-butanol, glycerin, polyethylene glycol (PEG), hexane, or glycol.

The active agent particles can be reduced in size in the presence of lysozyme. Alternatively, the active agent particles can be contacted with lysozyme after attrition. One or more secondary surface stabilizers may also be added before or after attrition. Other compounds, such as a diluent, can be added to the active agent/surface stabilizer composition during the size reduction process. Dispersions can be manufactured continuously or in a batch mode.

2. Precipitation to Obtain Nanoparticulate Active Agent Compositions Another method of forming the desired nanoparticulate composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving the poorly soluble active agent in a suitable solvent; (2) adding the formulation from step (1) to a solution comprising lysozyme and optionally one or more secondary surface stabilizers, to form a clear solution; and (3) precipitating the formulation from step (2) using an appropriate non-solvent. The method can be followed by removal of any formed salt, if present, by dialysis or diafiltration and concentration of the dispersion by conventional means.

3. Homogenization to Obtain Nanoparticulate Active Agent Compositions

Exemplary homogenization methods of preparing active agent nanoparticulate compositions are described in U.S. Pat. No. 5,510,118, for "Process of Preparing Therapeutic Compositions Containing Nanoparticles."

Such a method comprises dispersing active agent particles in a liquid dispersion medium in which active agent is poorly soluble, followed by subjecting the dispersion to homogenization to reduce the particle size of the active agent to the desired effective average particle size. The active agent particles can be reduced in size in the presence of lysozyme and, if desired, one or more additional surface stabilizers. Alternatively, the active agent particles can be contacted with lysozyme and, if desired, one or more additional surface stabilizers either before or after attrition. Other compounds, such as a diluent, can be added to the active agent/lysozyme composition either before, during, or after the size reduction process. Dispersions can be manufactured continuously or in a batch mode.

C. Methods of Using Nanoparticulate Active Agent Formulations The nanoparticulate compositions of the present invention can be administered to humans and animals via any conventional means including, but not limited to, orally, rectally, ocularly, parenterally (intravenous, intramuscular, or subcutaneous), intracisternally, pulmonary, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include capsules, tablets, pills, powders, and granules. In such solid dosage forms, the active agent is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active agent, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active agent in the nanoparticulate compositions of the invention may be varied to obtain an amount of active agent that is effective to obtain a desired therapeutic response for a particular composition and method of administration. The selected dosage level therefore depends upon the desired therapeutic effect, the route of administration, the potency of the administered active agent, the desired duration of treatment, and other factors.

Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered active agent, rates of absorption and excretion, combination with other active agents, and the severity of the particular disease being treated.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

In the examples that follow, the value for D50 is the particle size below which 50% of the active agent particles fall. Similarly, D90 is the particle size below which 90% of the active agent particles fall.

The formulations in the examples that follow were also investigated using a light microscope. Here, "stable" nanoparticulate dispersions (uniform Brownian motion) were readily distinguishable from "aggregated" dispersions (relatively large, nonuniform particles without motion).

EXAMPLE 1

The purpose of this example was to prepare nanoparticulate formulations of naproxen using different proteins as surface stabilizers.

Naproxen is an anti-inflammatory, analgesic, and antipyretic having the following chemical structure:

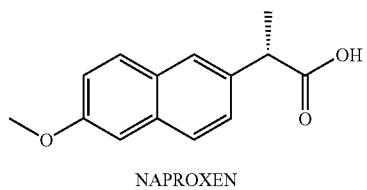

NAPROXEN

The compound has a molecular weight of 230.3 g, and a solubility in water of 16 µg/mL at pH 2 and 3.2 mg/mL at pH 7.5.

An aqueous dispersion of 1 wt. % protein surface stabilizer (see Table 1, below) and 5 wt. % naproxen was charged into a 10 cc batch chamber of a NanoMill® (Elan Pharmaceutical Technologies, Inc.) (See e.g., WO 00/72973 for "Small-Scale Mill and Method Thereof." Milling was conducted at 5000 rpm at 5° C. The results are shown below in Table 1.

TABLE 1

| Protein | Mean Particle Size (nm) | D50 Particle Size (nm) | D90 Particle Size (nm) | Microscope |
|---|---|---|---|---|
| fibrinogen | 18651 | 16189 | 32027 | Aggregated |
| γ-globulin | 24453 | 16201 | 49416 | Aggregated |
| albumin | 13559 | 11073 | 20974 | Aggregated |
| casein | 22768 | 11852 | 59611 | Aggregated |
| lysozyme | 81 | 78 | 114 | Stable |

The results demonstrate that only lysozyme was capable of functioning as a surface stabilizer to form a stable nanoparticulate composition of naproxen. Nanoparticulate compositions of naproxen and lysozyme had a mean particle size of 81 nm, with a D50 and D90 of 78 nm and 114 nm, respectively.

In contrast, every other protein stabilizer resulted in naproxen compositions having large particle sizes (i.e., mean particle sizes of about 13.6 to 22.8 microns, D50 particle sizes of 11.1 to 16.2 microns, and D90 particle sizes of 21.0 to 59.6 microns).

EXAMPLE 2

The purpose of this example was to prepare nanoparticulate formulations of the x-ray contrast agent benzoic acid, 3,5-bis(acetylamino)-2,4,6-triodo-4-(ethyl-3-ethoxy-2-butenoate) ester (WIN 68209) using different protein surface stabilizers.

WIN 68209 has the following chemical structure:

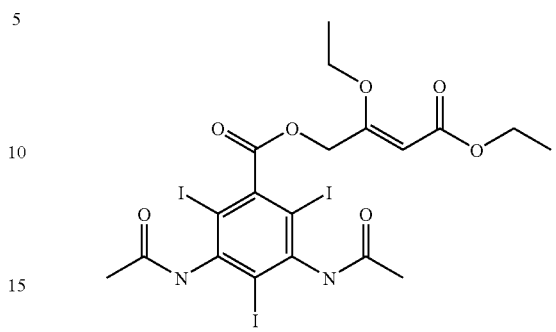

An aqueous dispersion of 1 wt. % protein surface stabilizer (see Table 2, below) and 5 wt. % WIN 68209 was charged into a 10 cc batch chamber of a NanoMill® (Elan Pharmaceutical Technologies, Inc.). Milling was conducted at 5500 rpm at 5° C. The results are shown below in Table 2.

TABLE 2

| Protein | Mean Particle Size (nm) | D50 Particle Size (nm) | D90 Particle Size (nm) | Microscope |
|---|---|---|---|---|
| fibrinogen | 6044 | 5695 | 10744 | Aggregated |
| γ-globulin | 4685 | 4334 | 8726 | Aggregated |
| albumin | 8290 | 7472 | 15137 | Aggregated |
| casein | 5407 | 4571 | 10094 | Aggregated |
| lysozyme | 82 | 78 | 116 | Stable |

The results demonstrate that only lysozyme was capable of functioning as a surface stabilizer to form a stable nanoparticulate composition of WIN 68209. Nanoparticulate compositions of WIN 68209 and lysozyme had a mean particle size of 82 nm, with a D50 and D90 of 78 nm and 116 nm, respectively.

In contrast, every other protein stabilizer resulted in WIN 68209 compositions having large particle sizes (i.e., mean particle sizes of about 4.7 to 8.3 microns, D50 particle sizes of 4.3 to 7.5 microns, and D90 particle sizes of 8.7 to 15 microns).

EXAMPLE 3

The purpose of this example was to prepare nanoparticulate formulations of itraconazole using different protein surface stabilizers.

Itraconazole is an antifungal compound having the following structure:

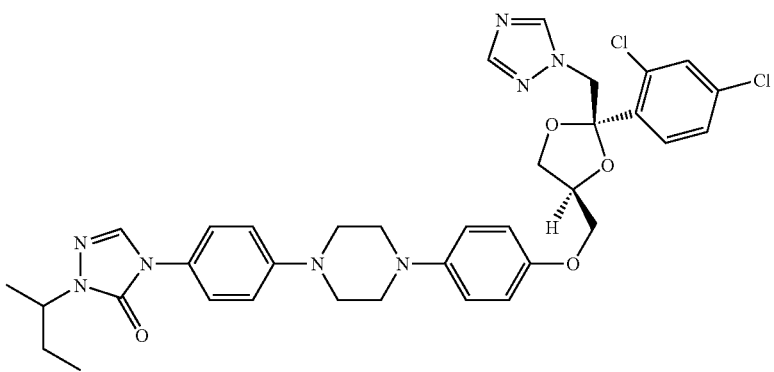

ITRACONAZOLE

An aqueous dispersion of 1 wt. % protein surface stabilizer (see Table 3, below) and 5 wt. % itraconazole (Wyckoff, Inc., South Haven, Mich.; Itraconazole Powder, Lot No. IT-01L01-P, Date of Manufacture: Nov. 4, 2001) was charged into a 10 cc batch chamber of a NanoMill® (Elan Pharmaceutical Technologies, Inc.). Milling was conducted at 5500 rpm at 5° C. The results are shown below in Table 3.

TABLE 3

| Protein | Mean (nm) | D50 (nm) | D90 (nm) | Microscope |
|---|---|---|---|---|
| fibrinogen | 4187 | 3745 | 7986 | Aggregated |
| γ-globulin | 10949 | 9284 | 20623 | Aggregated |
| albumin | 9219 | 7963 | 18969 | Aggregated |
| casein | 6289 | 5735 | 11222 | Aggregated |
| lysozyme | 930 | 450 | 1937 | Stable |

The results demonstrate that only lysozyme was capable of functioning as a surface stabilizer to form a stable nanoparticulate composition of itraconazole. Nanoparticulate compositions of itraconazole and lysozyme had a mean particle size of 930 nm, with a D50 and D90 of 450 nm and 1937 nm, respectively.

In contrast, every other protein stabilizer resulted in itraconazole compositions having large particle sizes (i.e., mean particle sizes of 4.2 to 10.9 microns, D50 particle sizes of 3.7 to 9.3 microns, and D90 particle sizes of 8.0 to 20.6 microns).

EXAMPLE 4

The purpose of this example was to prepare nanoparticulate formulations of prednisolone using different protein surface stabilizers. Prednisolone, a steroid hormone, is a dehydrogenated analogue of cortisol (hydrocortisone).

An aqueous dispersion of 1 wt. % protein surface stabilizer (see Table 4, below) and 5 wt. % prednisolone acetate was charged into a 10 cc batch chamber of a NanoMill® (Elan Pharmaceutical Technologies, Inc.). Milling was conducted at 5500 rpm at 5° C. The results are shown below in Table 4.

TABLE 4

| Protein | Mean (nm) | D50 (nm) | D90 (nm) | Microscope |
|---|---|---|---|---|
| fibrinogen | 5356 | 5221 | 8910 | Aggregated |
| γ-globulin | 5008 | 4801 | 8895 | Aggregated |
| albumin | 27817 | 18120 | 58730 | Aggregated |
| casein | 13394 | 4173 | 13278 | Aggregated |
| lysozyme | 143 | 139 | 191 | Stable |

The results demonstrate that only lysozyme was capable of functioning as a surface stabilizer to form a stable nanoparticulate composition of prednisolone acetate. Nanoparticulate compositions of prednisolone acetate and lysozyme had a mean particle size of 143 nm, with a D50 and D90 of 139 nm and 191 nm, respectively.

In contrast, every other protein stabilizer resulted in prednisolone acetate compositions having large particle sizes (i.e., mean particle sizes of 5.0 to 27.8 microns, D50 particle sizes of 4.8 to 18.1 microns, and D90 particle sizes of 8.9 to 58.7 microns).

EXAMPLE 5

The purpose of this example was to prepare nanoparticulate formulations of budesonide using different protein surface stabilizers. Budesonide, which is a corticosteroid, has the following chemical structure:

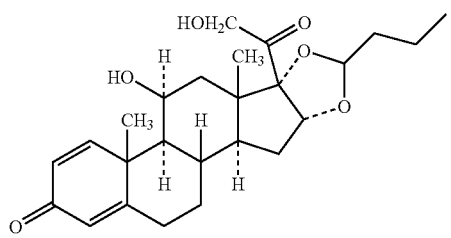

An aqueous dispersion of 1 wt. % protein surface stabilizer (see Table 5, below) and 5 wt. % budesonide was charged into a 10 cc batch chamber of a NanoMill® (Elan Pharmaceutical Technologies, Inc.). Milling was conducted at 5500 rpm at 5° C. The results are shown below in Table 5.

TABLE 5

| Protein | Mean (nm) | D50 (nm) | D90 (nm) | Microscope |
|---|---|---|---|---|
| fibrinogen | 5113 | 4566 | 9594 | Aggregated |
| γ-globulin | 6168 | 4703 | 11786 | Aggregated |
| albumin | 6946 | 5826 | 14160 | Aggregated |
| casein | 16302 | 6340 | 31346 | Aggregated |
| lysozyme | 393 | 328 | 565 | Stable |

The results demonstrate that only lysozyme was capable of functioning as a surface stabilizer to form a stable nanoparticulate composition of budesonide. Nanoparticulate compositions of budesonide and lysozyme had a mean particle size of 393 nm, with a D50 and D90 of 328 nm and 565 nm, respectively.

In contrast, every other protein stabilizer resulted in budesonide composition having large particle sizes (i.e., mean particle sizes of 5.1 to 16.3 microns, D50 particle sizes of 4.6 to 6.3 microns, and D90 particle sizes of 9.6 to 31.3 microns).

EXAMPLE 6

The purpose of this example was to prepare nanoparticulate formulations of lutein using lysozyme as a protein surface stabilizer. Lutein is a carotenoid found in vegetables and fruits. Lutein acts as an antioxidant, protecting cells against the damaging effects of free radicals. The compound has the chemical formula $C_{40}H_{52}O_2$ and a molecular weight of 568.88.

An aqueous dispersion of 1 wt. % lysozyme and 5 wt. % lutein was charged into a 10 cc batch chamber of a NanoMill® (Elan Pharmaceutical Technologies, Inc.). Milling was conducted at 5500 rpm at 5° C. The results are shown below in Table 6.

TABLE 6

| Protein | Mean (nm) | D50 (nm) | D90 (nm) | Microscope |
|---|---|---|---|---|
| lysozyme | 561 | 534 | 800 | Stable |

The results demonstrate that lysozyme was capable of functioning as a surface stabilizer to form a stable nanoparticulate composition of lutein. Nanoparticulate compositions of lutein and lysozyme had a mean particle size of 561 nm, with a D50 and D90 of 534 nm and 800 nm, respectively.

EXAMPLE 7

The purpose of this example was to prepare nanoparticulate formulations of various active pharmaceutical ingredient (API) compounds using lysozyme as a surface stabilizer.

An aqueous dispersion of 1 wt. % lysozyme (see Table 7, below) and 5 wt. % API was charged into either a NanoMill® equipped with a 10 cc batch chamber, or a DynoMill® (Type: KDL; Mfg.: Willy Bachofen, Basel, Switzerland) equipped with a 150 cc batch chamber. In the case of the NanoMill®, the mill speeds ranged from 2000 to 5500 rpm, while in the DynoMill®, milling was conducted at 4200 rpm. In both mills, the temperature was maintained at 5° C., while the total mill time varied from 0.5 to 2 hours. Following milling, the mean particle size, D50, and D90 were measured for each API milled sample. Each milled composition was also evaluated via a microscope to detect any aggregation. The results are shown below in Table 7.

TABLE 7

| API | Mean (nm) | D50 (nm) | D90 (nm) | Micro-scope | Mill | Mill Speed (rpm) | Mill Time (hr) |
|---|---|---|---|---|---|---|---|
| Compound A | 141 | 119 | 228 | Stable | Nano | 5500 | 2 |
| Compound B | 191 | 183 | 265 | Stable | Nano | 5500 | 1 |
| Compound C | 201 | 180 | 289 | Stable | Nano | 5500 | 2 |
| Compound D | 795 | 384 | 1948 | Stable | Nano | 5500 | 0.5 |
| Compound E | 338 | 304 | 501 | Stable | Nano | 5500 | 1 |
| Compound F | 110 | 104 | 169 | Stable | Nano | 5500 | 0.5 |
| Compound G | 264 | 252 | 352 | Stable | Nano | 5500 | 0.5 |
| Policosanol | 1357 | 553 | 3599 | Stable | Nano | 5500 | 2 |
| Benzoyl Peroxide | 122 | 110 | 196 | Stable | Nano | 5500 | 1 |
| Triamcinolone | 114 | 107 | 172 | Stable | Nano | 2500 | 0.5 |
| Paclitaxel | 141 | 130 | 190 | Stable | Nano | 4000 | 0.5 |
| Barium Sulfate | 277 | 268 | 377 | Stable | Dyno | 4200 | 1.5 |
| Ketoprofen | 85 | 84 | 114 | Stable | Dyno | 4200 | 1 |

The results demonstrate that lysozyme is capable of functioning as a surface stabilizer to form a stable nanoparticulate composition with each of the API compounds. Nanoparticulate compositions of the various API compounds and lysozyme had mean particles sizes ranging from 85 to 1357 nm, with D50 and D90 sizes ranging from 84 to 553 nm and 114 to 3599 nm, respectively.

EXAMPLE 8

The purpose of this example was to prepare a nanoparticulate dispersion of fluticasone propionate utilizing lysozyme as a surface stabilizer.

Fluticasone propionate is a synthetic, trifluorinated, corticosteroid having the chemical name of S-fluoromethyl-6α,9-difluoro-11β-hydroxy-16α-methyl-3-oxoandrosta-1,4-diene-17β-carbothioate, 17-propionate, and the empirical formula $C_{25}H_{31}F_3O_5S$. It is practically insoluble in water.

A mixture of 5% w/w fluticasone propionate and 2% lysozyme was milled for 30 min. under high energy milling conditions in a NanoMill® (Elan Drug Delivery, Inc.) equipped with a 18 cc batch chamber. 500 μm polymeric attrition media (The Dow Chemical Co., Midland, Mich.) was utilized in the milling process.

Particle size analysis of the milled fluticasone propionate composition, conducted using a Horiba LA-910 particle size analyzer (Irvine, Calif.) showed a final fluticasone propionate mean particle size of 311 nm.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A nanoparticulate composition comprising a nanoparticle of at least one active agent having lysozyme as a stabilizer adsorbed on the surface of said nanopanicle of said active agent, wherein said lysozyme is in an amount sufficient to maintain the active agent particles at an effective average particle size of less than about 2000 nm.

2. The composition of claim 1, wherein the at least one active agent is selected from the group consisting of a drug, vitamin, herb, cosmetic agent, coloring agent, flavor agent, fragrance agent, sunscreen, moisturizer, deodorant, hair conditioner agent, hair dye, hair spray agent, hair cosmetic agent, hair cleanser agent, depilatory agent, insecticide, fertilizer, pesticide, herbicide, germicide, and plant growth regulating agent.

3. The composition of claim 1, wherein the at least one active agent is selected from the group consisting of proteins, peptides, nutraceuticals, carotenoids, anti-obesity agents, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, blood products and substitutes, cardiac inotropic agents, contrast media, cough suppressants, diagnostic agents, diagnostic imaging agents, diuretics, dopaminergics, haemostatics, immunological agents, lipid regulating agents, muscle relaxants, parasympathomimetics, parathyroid calcitonin and biphosphonates, prostaglandins, radio-pharmaceuticals, sex hormones, antiallergic agents, stimulants and anoretics, sympathomimetics, thyroid agents, vasodilators, xanthines, acne medication, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, and respiratory illness therapies associated with acquired immune deficiency syndrome.

4. The composition of claim 1, wherein the composition is formulated for administration selected from the group consisting of vaginal, ocular, nasal, buccal, oral, colonic, topical, and parenteral administration.

5. The composition of claim 1, wherein the at least one active agent is present in an amount selected from the group consisting of from about 99.5% to about 0.001%, from about 95% to about 0.1%, and from about 90% to about 0.5%, by weight based on the total combined weight of the active agent and surface stabilizer, not including other excipients.

6. The composition of claim 1, wherein said lysozyme is present in an amount selected from the group consisting of from about 0.5% to about 99.999% from about 5.0% to about 99.9%, and from about 10% to about 99.5%, by weight, based on the total combined dry weight of the active agent and said lysozyme, not including other excipients.

7. The composition of claim 1, wherein the at least one active agent is selected from the group consisting of a crystalline phase, an amorphous phase, a semi-amorphous phase, a semi-crystalline phase, and mixtures thereof.

8. The composition of claim 1, further comprising at least one secondary surface stabilizer which is not said lysozyine.

9. The composition of claim 1, wherein the effective average particle size of the nanoparticulate composition is selected from the group consisting of less than about 1900 nm, less than about 1800 nm, less than about 1700 nm, less than about 1600 nm, less than about 1500 nm, less than about 1000 nm, less than about 1400 nm, less than about 1300 nm, less than about 1200 nm, less than about 1100 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

10. The composition of claim 1, wherein the composition further comprises one or more pharmaceutically acceptable excipients, carriers, or a combination thereof.

11. The composition of claim 1, wherein the composition adsorbs to a biological surface selected from the group consisting of an insect, teeth, bone, nails, chitin, feathers, scales, mucous, skin, hair, and plant tissue.

12. The composition of claim 1 in a dry powder form.

13. The composition of claim 1, wherein the active agent is fluticasone propionate.

14. The composition of claim 8, wherein the secondary surface stabilizer is selected from the group consisting of an anionic surface stabilizer, a cationic surface stabilizer, a zwitterionic surface stabilizer, a non-ionic surface stabilizer, and an ionic surface stabilizer.

15. The composition of claim 9, wherein at least about 70%, at least about 90%, or at least about 95% of the active agent particles have a particle size less than the effective average particle size.

16. The composition of claim 9, wherein the active agent is fluticasone propionate.

17. The composition of claim 14, wherein the at least one secondary surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and random copolymers of vinyl acetate and vinyl pyrrolidone.

18. The composition of claim 14, wherein the at least one cationic surface stabilizer is selected from the group consisting of a polymer, a biopolymer, a polysaccharide, a cellulosic, an alginate, a nonpolymeric compound, a phospholipid, zwitterionic stabilizers, poly-n-methylpyridinium, anthryul pyridinium chloride, chitosan, polylysine, polyvinylimidazole, polybrene, polymethylmethacrylate trimethylammoniumbromide bromide (PMMTMABr), hexyidesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt), Poly(2-methacryloxyethyl trimethylammonium bromide), poloxamines, lysozyme, alginic acid, carrageenan, and water soluble resins.

19. The composition of claim 14, wherein the at least one cationic surface stabilizer is selected from the group consisting of cationic lipids, sulfonium, phosphonium, quartemary ammonium compounds, stearyltrimethylammonium chloride, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$dimethyl hydroxyethyl ammonium chloride, $C_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts, amines, protonated quatemary acrylamides, methylated quaternary polymers, and cationic guar.

20. The composition of claim 18, wherein the cationic surface stabilizer is a nonpolymeric compound selected from the group consisting of benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium beazoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyQuaternium-1, procainehydrochloride, cocobetaine, stearalkonium bentonite, stearalkoniumhectorite, stearyl trihydroxyethyl propylenediamine dihydrofluoride, tallowtrimonium chloride, and hexadecyltrimethyl ammonium bromide.

21. The composition of claim 19, wherein the amine is selected from the group consisting of alkylamines, dialkylamines, alkanolamines, polyethylenepolyamines, N,N-dialkylaminoalkyl acrylates, vinyl pyridine, amine salts, lauryl amine acetate, stearyl amine acetate, alkylpyridinium salt, alkylimidazolium salt, amine oxides, and, imide azolinium salts.

22. A method of making a nanoparticulate composition comprising a nanoparticle of at least one active agent having lysozyme as a stabilizer adsorbed on the surface of said nanoparticle of said active agent, wherein said lvsozvme is absorbed on the surface of said nanoparticle of said active agent in an amount sufficient to maintain the active agent particles at an effective average particle size of less than about 2000 nm,
said method comprising contacting said a nanoparticle of at least one active agent with lysozyme for a time and under conditions sufficient to provide a nanoparticulate active agent/lysozyme composition having an effective average particle size of less than about 2000 nm.

23. The method of claim 22, wherein said contacting comprising grinding.

24. The method of claim 22, wherein said contacting comprises homogenizing.

25. The method of claim 22, wherein said contacting comprises:
(a) dissolving said active agent particles in a solvent;
(b) adding the resulting active agent solution to a solution comprising said lysozyme; and
(c) precipitating the solubilized said active agent/said lysozyme composition by the addition thereto of a nonsolvent.

26. The method of claim 22, wherein the at least one active agent is selected from the group consisting of a drug, vitamin, herb, cosmetic agent, coloring agent, flavor agent, fragrance agent, sunscreen, moisturizer, deodorant, hair conditioner agent, hair dye, hair spray agent, hair cosmetic agent, hair cleanser agent, depilatory agent, insecticide, fertilizer, pesticide, herbicide, germicide, and plant growth regulating agent.

27. The method of claim 22, wherein the at least one active agent is selected from the group consisting of proteins, peptides, nutraceuticals, carotenoids, anti-obesity agents, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, β-adrenoceptor blocking agents, blood products and substitutes, cardiac inotropic agents, contrast media, cough suppressants, diagnostic agents, diagnostic imaging agents, diuretics, dopaminergics, haemostatics, immunological agents, lipid regulating agents, muscle relaxants, parasyinpathomimetics, parathyroid calcitonin and biphosphonates, prostaglandins, radio-pharmaceuticals, sex hormones, anti-allergic agents, stimulants and anoretics, sympathomimetics, thyroid agents, vasodilators, xanthines, acne medication, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, and respiratory illness therapies associated with acquired immune deficiency syndrome.

28. The method of claim 22, wherein the at least one active agent is present in an amount selected from the group consisting of from about 99.5% to about 0.001%, from about 95% to about 0.1%, and from about 90% to about 0.5%, by weight based on the total combined weight of the active agent and surface stabilizer, not including other excipients.

29. The method of claim 22, wherein said lysozyme is present in an amount selected from the group consisting of from about 0.5% to about 99.999%, from about 5.0% to about 99.9%, and from about 10% to about 99.5%, by weight, based on the total combined dry weight of the active agent and said lysozyme, not including other excipients.

30. The method of claim 22, wherein the at least one active agent is selected from the group consisting of a crystalline phase, an amorphous phase, a semi-amorphous phase, a semi-crystalline phase, and mixtures thereof.

31. The method of claim 22, further comprising at least one secondary surface stabilizer which is not said lysozyine.

32. The method of claim 22, wherein the effective average particle size of the nanoparticulate composition is selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

33. The method of claim 22, wherein the active agent is fluticasone propionate.

34. The method of claim 23, wherein said grinding comprising wet grinding.

35. The method of claim 31, wherein the secondary surface stabilizer is selected from the group consisting of an anionic surface stabilizer, a cationic surface stabilizer, a zwitterionic surface stabilizer, a non-ionic surface stabilizer, and an ionic surface stabilizer.

36. The method of claim 32, wherein at least about 70%, at least about 90%, or at least about 95% of the active agent particles have a particle size less than the effective average particle size.

37. The method of claim 35, wherein the at least one secondary surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and random copolymers of vinyl acetate and vinyl pyrrolidone.

38. The method of claim 35, wherein the at least one cationic surface stabilizer is selected from the group consisting of a polymer, a biopolymer, a polysaccharide, a cellulosic, an alginate, a nonpolymeric compound, a phospholipid, zwitterionic stabilizers, poly-n-methylpyridinium, anthryul pyridinium chloride, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt), Poly(2-methacryloxyethyl trimethylammonium bromide), poloxamines, lysozyme, alginic acid, carrageenan, and water soluble resins.

39. The method of claim 35, wherein the at least one cationic surface stabilizer is selected from the group consisting of cationic lipids, sulfonium, phosphonium, quarternary ammonium compounds, stearyltrimethylammonium chloride, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$dimethyl hydroxyethyl ammonium chloride, $C_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylamonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts, amines, protonated quatemary acrylamides, methylated quaternary polymers, and cationic guar.

40. The method of claim 38, wherein the cationic surface stabilizer is a nonpolymeric compound selected from the group consisting of benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyQuaternium-1, procainehydrochloride, cocobetaine, stearalkonium bentonite, stearalkoniumhectorite, stearyl trihydroxyethyl propylenediamine dihydrofluoride, tallowtrimonium chloride, and hexadecyltrimethyl ammonium bromide.

41. The method of claim 39, wherein the amine is selected from the group consisting of alkylamines, dialkylamines, alkanolamines, polyethylenepolyamines, N,N-dialkylaminoalkyl acrylates, vinyl pyridine, amine salts, lauryl amine acetate, stearyl amine acetate, alkylpyridinium salt, alkylimidazolium salt, amine oxides, and, imide azolinium salts.

42. A method of treating a mammal in need thereof with a nanoparticulate composition comprising:
(a) a nanoparticle of at least one active agent; and
(b) lysozyme as a surface stabilizer absorbed on associated with the surface of the nanoparticulate active agent,
wherein the method comprises administering to said mammal in need thereof a therapeutically effective amount of said nanoparticulate composition, wherein the active agent particles have an effective average particle size of less than about 2000 nm.

43. The method of claim 42, wherein the at least one active agent is selected from the group consisting of a drug, vitamin, herb, cosmetic agent, coloring agent, flavor agent, fragrance agent, sunscreen, moisturizer, deodorant, hair conditioner agent, hair dye, hair spray agent, hair cosmetic agent, hair cleanser agent, depilatory agent, insecticide, fertilizer, pesticide, herbicide, germicide, and plant growth regulating agent.

44. The method of claim 42, wherein the at least one active agent is selected from the group consisting of proteins, peptides, nutraceuticals, carotenoids, anti-obesity agents, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, β-adrenoceptor blocking agents, blood products and substitutes, cardiac inotropic agents, contrast media, cough suppressants, diagnostic agents, diagnostic imaging agents, diuretics, dopaminergics, haemostatics, immunological agents, lipid regulating agents, muscle relaxants, parasyinpathomimetics, parathyroid calcitonin and biphosphonates, prostaglandins, radio-pharmaceuticals, sex hormones, anti-allergic agents, stimulants and anoretics, sympathomimetics, thyroid agents, vasodilators, xanthines, acne medication, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, and respiratory illness therapies associated with acquired immune deficiency syndrome.

45. The method of claim 42, wherein the at least one active agent is present in an amount selected from the group consisting of from about 99.5% to about 0.00 1%, from about 95% to about 0.1%, and from about 90% to about 0.5%, by weight based on the total combined weight of the active agent and surface stabilizer, not including other excipients.

46. The method of claim 42, wherein said lysozyme is present in an amount selected from the group consisting of from about 0.5% to about 99.999%, from about 5.0% to about 99.9%, and from about 10% to about 99.5%, by weight, based on the total combined dry weight of the active agent and said lysozyme, not including other excipients.

47. The method of claim 42, wherein the at least one active agent is selected from the group consisting of a crystalline phase, an amorphous phase, a semi-amorphous phase, a semi-crystalline phase, and mixtures thereof.

48. The method of claim 42, further comprising at least one secondary surface stabilizer which is not said lysozyine.

49. The method of claim 42, wherein the effective average particle size of the nanoparticulate composition is selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

50. The method of claim 42, wherein the active agent is fluticasone propionate.

51. The method of claim 48, wherein the secondary surface stabilizer is selected from the group consisting of an anionic surface stabilizer, a cationic surface stabilizer, a zwitterionic surface stabilizer, a non-ionic surface stabilizer, and an ionic surface stabilizer.

52. The method of claim 48, wherein the at least one cationic surface stabilizer is selected from the group consisting of a polymer, a biopolymer, a polysaccharide, a cellulosic, an alginate, a nonpolymeric compound, a phospholipid, zwitterionic stabilizers, poly-n-methylpyridinium, anthryul pyridinium chloride, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt), Poly(2-methacryloxyethyl trimethylammonium bromide), poloxamines, lysozyme, alginic acid, carrageenan, and water soluble resins.

53. The method of claim 48, wherein the at least one cationic surface stabilizer is selected from the group consisting of cationic lipids, sulfonium, phosphonium, quartemary ammonium compounds, stearyltrimethylammonium chloride, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$-dimethyl hydroxyethyl ammonium chloride, $C_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts, amines, protonated quaternary acrylamides, methylated quaternary polymers, and cationic guar.

54. The method of claim 49, wherein at least about 70%, at least about 90%, or at least about 95% of the active agent particles have a particle size less than the effective average particle size.

55. The composition of claim 51, wherein the at least one secondary surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylgiucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl-β-D-thioglucopyranoside; and random copolymers of vinyl acetate and vinyl pyrrolidone.

56. The method of claim 52, wherein the cationic surface stabilizer is a nonpolymeric compound selected from the group consisting of benzalkonium chloride, a carbonium compound, a phosphonium compound, an oxonium compound, a halonium compound, a cationic organometallic compound, a quartemary phosphorous compound, a pyridinium compound, an anilinium compound, an ammonium compound, a hydroxylammonium compound, a primary ammonium compound, a secondary ammonium compound, a tertiary ammonium compound, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

57. The method of claim 53, wherein the amine is selected from the group consisting of alkylamines, dialkylamines, alkanolamines, polyethylenepolyamines, N,N-dialkylaminoalkyl acrylates, vinyl pyridine, amine salts, lauryl amine acetate, stearyl amine acetate, alkylpyridinium salt, alkylimidazolium salt, amine oxides, and, imide azolinium salts.

\* \* \* \* \*

UNITED STATES PATENT AND TRADEMARK OFFICE
CERTIFICATE OF CORRECTION

PATENT NO. : 7,459,283 B2  Page 1 of 1
APPLICATION NO. : 10/357514
DATED : December 2, 2008
INVENTOR(S) : Wertz et al.

It is certified that error appears in the above-identified patent and that said Letters Patent is hereby corrected as shown below:

On the title page,

Item [*] Notice: Subject to any disclaimer, the term of this patent is extended or adjusted under 35 USC 154(b) by 780 days Delete the phrase "by 780 days" and insert -- by 1,252 days --

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,459,283 B2  Page 1 of 1
APPLICATION NO. : 10/357514
DATED : December 2, 2008
INVENTOR(S) : Christian F. Wertz, Niels P. Ryde and H. William Bosch It is certified that error appears in the above-identified patent and that said Letters Patent is hereby corrected as shown below:

ON THE TITLE PAGE:

Please delete the following under Item (*) Notice:

"This patent is subject to a terminal disclaimer."

Signed and Sealed this

Twenty-second Day of June, 2010

David J. Kappos
*Director of the United States Patent and Trademark Office*